(12) United States Patent
Flanagan

(10) Patent No.: US 11,751,938 B2
(45) Date of Patent: Sep. 12, 2023

(54) ABLATION CATHETER WITH BLOOD PERFUSION SENSOR

(71) Applicant: Boston Scientific Scimed, Inc., Maple Grove, MN (US)

(72) Inventor: Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 629 days.

(21) Appl. No.: 16/824,491

(22) Filed: Mar. 19, 2020

(65) Prior Publication Data

US 2020/0297414 A1 Sep. 24, 2020

Related U.S. Application Data

(60) Provisional application No. 62/822,188, filed on Mar. 22, 2019.

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/0084* (2013.01); *A61B 5/0261* (2013.01); *A61B 5/0295* (2013.01); *A61B 5/6852* (2013.01); *A61B 2018/00351* (2013.01); *A61B 2018/00577* (2013.01); *A61B 2018/00666* (2013.01);
(Continued)

(58) Field of Classification Search
CPC ...... A61B 18/1492; A61B 2017/00057; A61B 2017/00066; A61B 2018/00351; A61B 2018/00577; A61B 2018/00666; A61B 2018/00863; A61B 2018/00934; A61B 2218/002; A61B 2505/05; A61B 5/0084;
(Continued)

(56) References Cited

U.S. PATENT DOCUMENTS 4,344,438 A * 8/1982 Schultz ................ A61B 5/1459
600/341
5,902,251 A * 5/1999 vanHooydonk ....... A61N 5/045
600/549
(Continued)

FOREIGN PATENT DOCUMENTS

WO 2018/039458 A1 3/2018

*Primary Examiner* — Michael F Peffley
*Assistant Examiner* — Amanda L Zink
(74) *Attorney, Agent, or Firm* — Nelson Mullins Riley & Scarborough LLP

(57) ABSTRACT

Methods and systems for performing ablation are disclosed. An example system for performing ablation on a tissue includes a catheter having at least one lumen in which a first optical fiber configured to carry a first light beam is disposed and a second optical fiber configured to carry a second light beam is disposed, and a processor being configured to measure a volume of blood within the target site of the tissue using a blood perfusion sensor, determine that the volume of blood within the target site is below a predetermined threshold based on one or more characteristics detected by the blood perfusion sensor, each characteristic being associated with at least one of the first light beam and the second light beam, and perform the ablation on the target site of the tissue when the volume of blood within the target site is below the predetermined threshold.

19 Claims, 4 Drawing Sheets

(51) Int. Cl.
　　　*A61B 5/026*　　　(2006.01)
　　　*A61B 5/0295*　　(2006.01)
　　　*A61B 18/00*　　　(2006.01)

(52) U.S. Cl.
　　　CPC .............. *A61B 2018/00863* (2013.01); *A61B 2018/00934* (2013.01)

(58) Field of Classification Search
　　　CPC ... A61B 5/0261; A61B 5/0295; A61B 5/4848; A61B 5/6852; A61B 5/6885
　　　See application file for complete search history.

(56) References Cited

U.S. PATENT DOCUMENTS

| | | | |
|---|---|---|---|
| 6,200,310 B1* | 3/2001 | Ben-Haim | A61N 5/0601 606/15 |
| 7,660,616 B1 | 2/2010 | Poore | |
| 7,840,246 B1 | 11/2010 | Poore | |
| 8,914,108 B2 | 12/2014 | Bornzin et al. | |
| 10,835,313 B2* | 11/2020 | Margallo Balbás | A61B 5/4848 |
| 2008/0033300 A1* | 2/2008 | Hoang | A61B 18/20 606/42 |
| 2011/0028837 A1* | 2/2011 | Byrd | A61B 5/0071 600/478 |

* cited by examiner

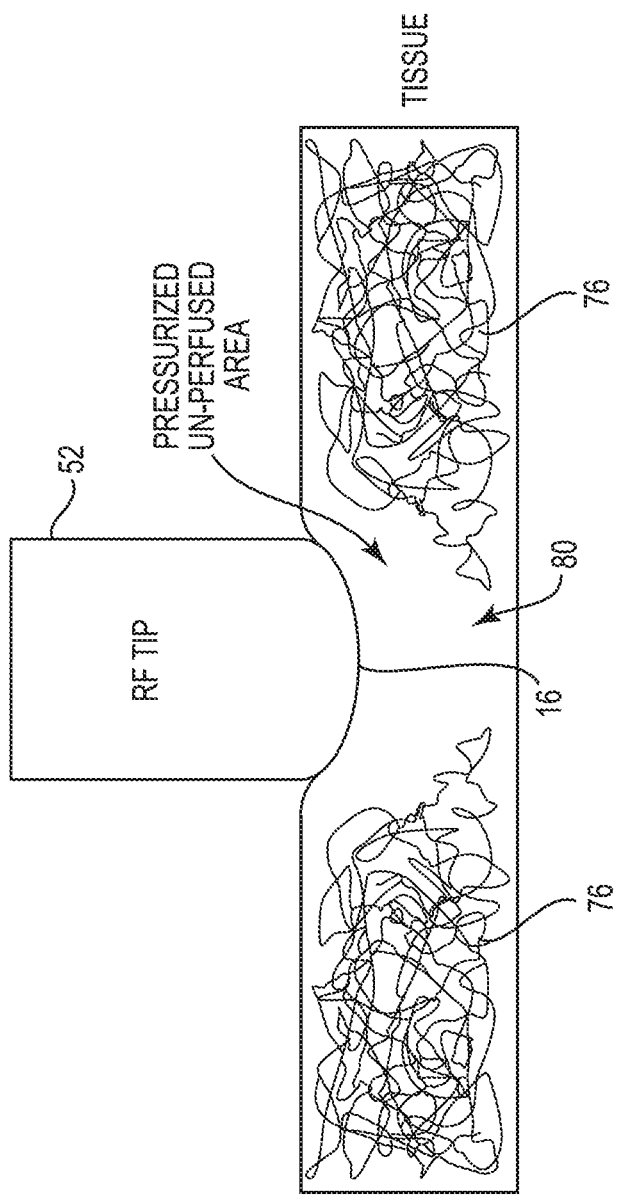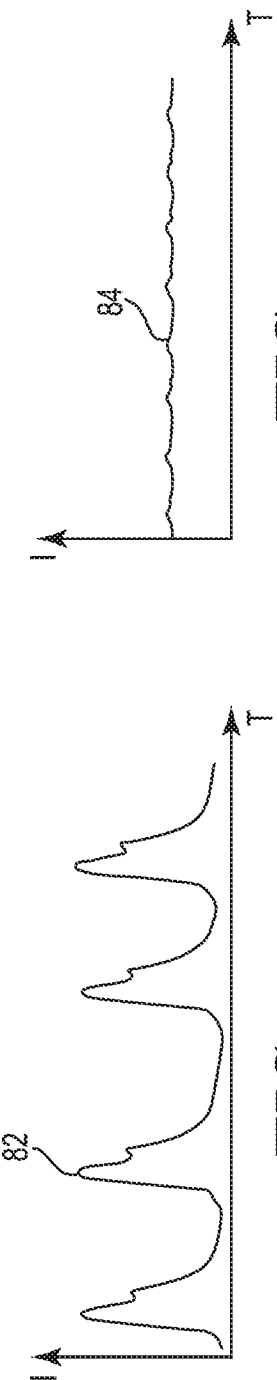
FIG. 3
FIG. 4
FIG. 5

ABLATION CATHETER WITH BLOOD PERFUSION SENSOR

CROSS REFERENCE TO RELATED APPLICATION

This application claims priority to Provisional Application No. 62/822,188, filed Mar. 22, 2019, which is herein incorporated by reference in its entirety.

TECHNICAL FIELD

The present disclosure relates to analyzing anatomical structures within the body. More specifically, the present disclosure relates to systems, methods, and devices for monitoring and assessing tissue ablation based on blood perfusion.

BACKGROUND

In ablation therapy, it is often necessary to determine various characteristics of body tissue at a target ablation site within the body. In interventional cardiac electrophysiology procedures, for example, it is often necessary for the physician to determine the condition of cardiac tissue at a target ablation site in or near the heart.

SUMMARY

This disclosure provides design, material, method, system and use alternatives for medical devices.

In Example 1, a system for performing ablation on a target tissue, the system comprising a catheter and a blood perfusion sensor. The catheter includes an elongate catheter body having a proximal end and an opposite distal end, and a catheter tip coupled to the distal end of the catheter body and configured to deliver ablative energy to the target tissue. The blood perfusion sensor is operatively coupled to the catheter tip and is configured to measure and generate an output representing a degree of blood perfusion within the target tissue when the catheter tip is in contact with the target tissue.

In Example 2, the medical system of Example 1, wherein the blood perfusion sensor comprises a light source configured to generate and transmit a first light beam to be directed from the catheter tip toward the target tissue, and a light detector configured to detect a second light beam that is reflected from the target tissue.

In Example 3, the medical system of Example 2, wherein the light source is a light-emitting diode and the light detector is a photodiode.

In Example 4, the medical system of any of Examples 2-3, wherein one or both of the light source and the light detector are disposed within the catheter tip.

In Example 5, the medical system of any of Examples 2-3, wherein the catheter further comprises an optical fiber disposed within the catheter body and the catheter tip and operatively connected to one or both of the light source and the light detector.

In Example 6, the medical system of any of any of Examples 2-3, wherein the catheter further comprises a first optical fiber disposed within the catheter body and the catheter tip and operatively connected to the light source, and a second optical fiber disposed within the catheter body and the catheter tip and operatively connected to the light detector.

In Example 7, the medical system of any of Examples 2-6, wherein the perfusion sensor is further configured to detect a change in the volume of blood within the target tissue resulting from a force applied to the target tissue by the catheter tip.

In Example 8, the medical system of Example 7, wherein the change in the volume of blood within the target tissue is measured based on a change in light absorption by the target tissue resulting from the force applied to the target tissue by the catheter tip.

In Example 9, the medical system of any of Examples 2-8, wherein the blood perfusion sensor is configured to measure an intensity value of the first light beam or the second light beam, and a corresponding time value.

In Example 10, the medical system of Example 9, wherein the blood perfusion sensor is further configured to calculate an average value of the intensity value to represent an overall intensity of the second light beam.

In Example 11, the medical system of Example 9, wherein the blood perfusion sensor is further configured to determine whether the intensity value is less than a predetermined threshold for a predetermined period.

In Example 12, the medical system of any of Examples 1-11, wherein the processor is further configured to assess a lesion formation at the target tissue based on comparison of the first light beam and the second light beam.

In Example 13, the system of any of Examples 1-12, wherein the first light beam is selectively transmitted at a predetermined wavelength.

In Example 14, the medical system of any of Examples 1-13, further comprising an ablation controller configured to generate and deliver the ablative energy to the catheter tip when the detected degree of blood perfusion in the target tissue is below a pre-determined threshold value.

In Example 15, the medical system of any of Examples 1-14, wherein the ablative energy is a radiofrequency current.

In Example 16, a method for performing ablation on a target tissue, the method comprising transmitting, using a light source, a first light beam to the target tissue, detecting, using a light detector, a second light beam reflected by the target tissue, measuring a volume of blood within the target site based on the second light beam, determining whether the volume of blood within the target tissue is below a predetermined threshold based on one or more characteristics relating to blood perfusion at the target site, each characteristic being associated with at least one of the first light beam or the second light beam, and performing the ablation on the target site of the tissue when the volume of blood within the target tissue is below the predetermined threshold.

In Example 17, the method of Example 16, further comprising operatively connecting both the light source and the light detector to a tip of the catheter.

In Example 18, the method of Example 16, further comprising measuring a change in the volume of blood within the target tissue based on a change in light absorption by the target site tissue.

In Example 19, the method of Example 16, wherein the one or more characteristics includes an intensity value of at least one of the first light beam or the second light beam, and a corresponding time value.

In Example 20, the method of Example 19, further comprising determining whether the intensity value is less than a predetermined threshold for a predetermined period.

In Example 21, the method of Example 16, further comprising selectively transmitting the first light beam at a predetermined wavelength.

In Example 22, a system for performing ablation on a target tissue, the system comprising a catheter and a blood perfusion sensor. The catheter includes an elongate catheter body having a proximal end and an opposite distal end, and a catheter tip coupled to the distal end of the catheter body and configured to deliver ablative energy to the target tissue. The blood perfusion sensor is operatively coupled to the catheter tip and configured to measure and generate an output representing a degree of blood perfusion within the target tissue when the catheter tip is in contact with the target tissue. The blood perfusion sensor comprises a light detector configured to detect light reflected from the target tissue during use.

In Example 23, the medical system of Example 22, further comprising a light source configured to generate and transmit a light beam to be directed from the catheter tip toward the target tissue.

In Example 24, the medical system of Example 23, wherein the light source is a light-emitting diode and the light detector is a photodiode.

In Example 25, the medical system of Example 23, wherein one or both of the light source and the light detector are disposed within the catheter tip.

In Example 26, the medical system of Example 23, wherein the catheter further comprises an optical fiber disposed within the catheter body and the catheter tip and operatively connected to one or both of the light source and the light detector.

In Example 27, the medical system of Example 23, wherein the catheter further comprises a first optical fiber disposed within the catheter body and the catheter tip and operatively connected to the light source, and a second optical fiber disposed within the catheter body and the catheter tip and operatively connected to the light detector.

In Example 28, the medical system of Example 23, wherein the blood perfusion sensor is further configured to detect a change in the volume of blood within the target tissue resulting from a force applied to the target tissue by the catheter tip.

In Example 29, the medical system of Example 28, wherein the change in the volume of blood within the target tissue is measured based on a change in light absorption by the target tissue resulting from a force applied to the target tissue by the catheter tip.

In Example 30, the medical system of Example 22, wherein the blood perfusion sensor is further configured to determine whether the blood volume within the target tissue is less than a predetermined threshold for a predetermined period.

In Example 31, the medical system of Example 22, further comprising an ablation controller configured to generate and deliver the ablative energy to the catheter tip when the measured degree of blood perfusion is below a pre-determined threshold value.

In Example 32, a system for performing ablation on a target tissue, the system comprising a catheter, a light source, a light detector, and a measurement processor. The catheter includes an elongate catheter body, a catheter tip, a first optical fiber and a second optical fiber. The elongate catheter body has a proximal end and an opposite distal end. The catheter tip is coupled to the distal end of the catheter body and configured to deliver ablative energy to the target tissue. The first optical fiber is disposed within the catheter body and the catheter tip, and the second optical fiber is disposed within the catheter body and the catheter tip. The light source is operatively connected to the first optical fiber and configured to generate and transmit a first light beam to be directed from the catheter tip toward the target tissue. The light detector is operatively connected to the second optical fiber and configured to detect a second light beam that is reflected from the target tissue. The measurement processor is operatively connected to the light detector and configured to measure and generate an output representing a degree of blood perfusion within the target tissue when the catheter tip is in contact with the target tissue.

In Example 33, the medical system of Example 32, wherein the light source is a light-emitting diode and the light detector is a photodiode.

In Example 34, the medical system of Example 32, wherein measurement processor is configured to measure a change in blood perfusion within the target tissue based on a change in the volume of blood within the target tissue resulting from a force applied to the target tissue by the catheter tip.

In Example 35, the medical system of Examples 32, further comprising an ablation controller configured to generate and deliver the ablative energy to the catheter tip when the measured degree of blood perfusion level in the target tissue is below a pre-determined threshold value.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The disclosure may be more completely understood in consideration of the following detailed description in connection with the accompanying drawings, in which:

FIG. 3 is a schematic diagram depicting an exemplary use of the ablation catheter shown in FIG. 2 in accordance with embodiments of the disclosed subject matter;

FIGS. 4 and 5 are exemplary graphical representations of changes in light absorption detected by the ablation catheter system of FIG. 1 in accordance with embodiments of the disclosed subject matter.

Figure 1:
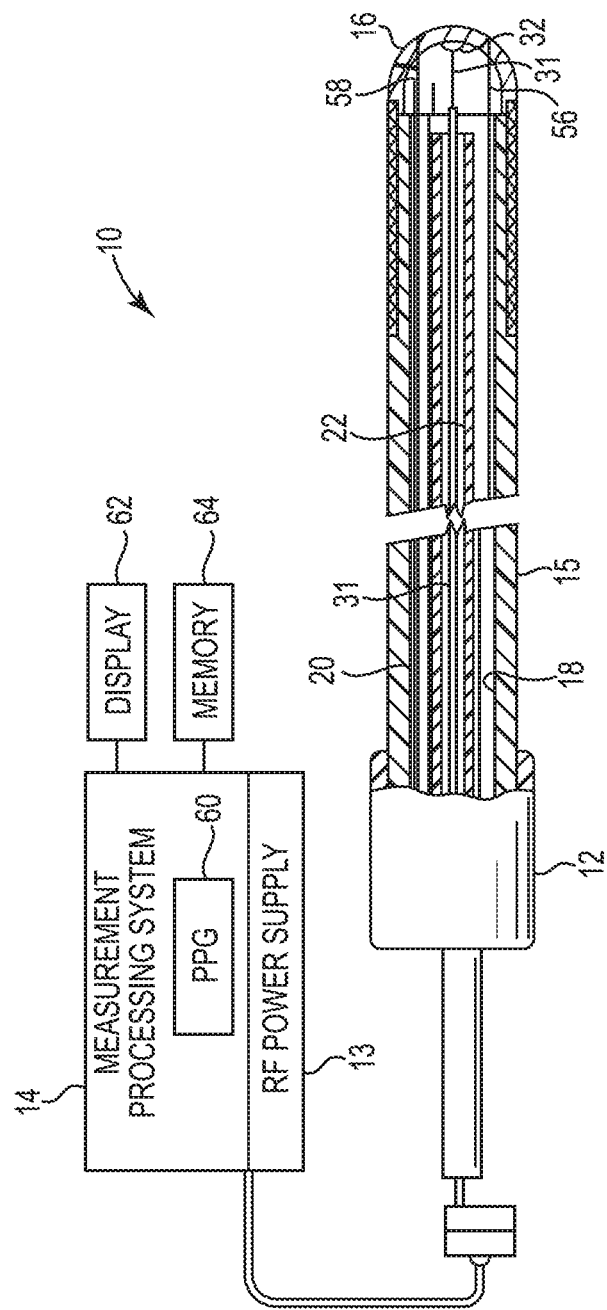
FIG. 1 is a schematic block diagram depicting an illustrative ablation catheter system in accordance with embodiments of the disclosed subject matter.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an example", "some examples", "other examples", etc., indicate that the example described may include one or more particular features, structures, and/or characteristics. However, such recitations do not necessarily mean that all examples include the particular features, structures, and/or characteristics. Additionally, when particular features, structures, and/or characteristics are described in connection with one example, it should be understood that such features, structures, and/or characteristics may also be used in connection with other examples whether or not explicitly described unless clearly stated to the contrary. Also, when particular features, structures, and/or characteristics are described in connection with one example, it is implicit that other examples may include less than all of the disclosed features, structures, and/or characteristics in all combinations.

The following detailed description should be read with reference to the drawings in which similar elements in different drawings are numbered the same. The drawings, which are not necessarily to scale, depict illustrative embodiments and are not intended to limit the scope of the disclosure.

RF energy can be used to ablate tissues, such as tissues in the heart, to form appropriate lesion barriers to stop a flow of abnormal currents. One exemplary apparatus for performing RF ablation is an RF ablation catheter with an ablative catheter tip. An internal electrode (e.g., the ablative tip of the RF ablation catheter) is placed inside the body, adjacent to the tissue which is to be ablated. An external electrode is placed on a skin surface. A power supply generates electrical power (e.g., a radio frequency current) which is communicated between the internal electrode and the external electrode so that the RF energy ablates the tissue in the vicinity of the internal electrode.

FIG. 1 is a simplified schematic of an illustrative RF ablation catheter system 10 configured to perform RF ablation on a tissue and measure the blood perfusion at a target site of the tissue (e.g., in the heart) and to perform the RF ablation at the target site based on the measured blood perfusion. The catheter system 10 includes a catheter 12, a power supply 13, and a measurement processing system 14. In various embodiments, the power supply is configured to supply high frequency energy to the catheter 12 to ablate the target tissue by forming one or more lesions at the target site. Additionally, the measurement processing system 14 is operatively coupled to the catheter 12 and is configured to derive, among other things, diagnostic information that can be provided to the clinician for use in performing the ablation procedure, as will be explained in detail below.

As shown, the catheter 12 includes a flexible elongate body 15 and an electrode tip 16 disposed at a distal end of the elongate body 15. In various embodiments, the elongate body 15 can be formed of any polymer material, whether now known or later developed, suitable for use in catheter construction. By way of example only, such polymers include polyurethane, polyether block amides, or comparable materials. The conductive electrode tip 16 can likewise be formed of any material suitable for ablation electrodes, such as, for example, stainless steel or platinum.

In the illustrated embodiment, disposed within the elongate body 15 is a first fiber lumen 18, a second fiber lumen 20, a wire lumen 22, and a lead wire 31. As shown, the lead wire 31 runs through the wire lumen 28 and is operatively connected to the conductive tip 16 at a juncture 32. It is emphasized, however, that the particular construction of the elongate body 15 and electrode tip 16 is not critical to the present disclosure, and thus the catheter 12 can include additional or fewer lumens or different configurations for the construction of the electrode tip 16 and the means of supplying RF power thereto.

Additionally, in various embodiments, the catheter 12 may be an irrigated design capable of receiving an irrigation fluid (e.g., saline), and the catheter system 10 may include an irrigation fluid supply system (not shown) configured to supply the fluid to the catheter 12. Irrigated RF ablation catheters are well known in the art, and thus need not be discussed further herein.

As further shown, the catheter 12 further includes a first optical fiber 56 disposed within the first fiber lumen 18 of the elongate body 15 and within the catheter electrode tip 16, and a second optical fiber 58 disposed within the second fiber lumen 20 of the elongate body 15 and also within the electrode tip 16. Each of the first and second optical fibers 56, 58 is configured to carry a light beam for use by the catheter system 10 in assessing a degree of blood perfusion in the target tissue to be ablated, as will be explained in greater detail elsewhere herein. In embodiments, both the first and second optical fibers 56, 58 are operatively coupled to the measurement processing system 14, which is configured to measure an volume of blood representative of an degree of blood perfusion at the target site while performing the RF ablation. Each optical fiber 56, 58 can be an optical probe configured to carry an optical signal between the measurement processing system 14 and the catheter 12. Although the optical fibers 56, 58 are shown separately in their respective lumens 18, 20, the optical fibers 56, 58 can be assembled in an integrated structure (e.g., a fiber assembly) that can be disposed in a single lumen, such as the wire lumen 22. In some embodiments, the optical fibers 56, 58 can be disposed in the center of the electrode tip 16. In various embodiments, the distal ends of the optical fibers 56, 58 can protrude slightly, be recessed from, or substantially flush with an outer surface of the electrode tip 16.

Also, in various embodiments, the catheter 12 may be configured such that the lumen 22 may carry a fluid (e.g., an irrigation fluid such as saline as used in an open-irrigated ablation catheter, as is known in the art) that exits proximate the ends of the optical fibers 56, 58 and aids in creating a clear light path between the optical fibers 56, 58 and a tissue surface.

In various embodiments, the measurement processing system 14 includes a blood perfusion sensor 60, such as a photoplethysmography (PPG) sensor, configured to measure the amount or volume of blood in the target tissue before, during, and after the RF ablation to monitor an effectiveness of the RF ablation. In embodiments, the blood perfusion sensor 60 measures a volume or an amount of blood in the tissue at any one time.

In embodiments, PPG refers to the technique of using a light source, a photodetector, and electronic or software processing of the light signal to output the measurement of a reflected light signal from the tissue. In embodiments, the blood perfusion sensor 60 is a photodetector, such as a photodiode, configured to sense light transmitted by the optical fiber 58. Alternatively, the blood perfusion sensor 60 may refer to a combination of light source (e.g., LED) and photodetector (e.g., photodiode), which may be incorporated into a single package with an electronic processor (e.g., an amplifier or a MAX30105 optical sensor manufactured by Maxim Integrated). In short, the various embodiments of the blood perfusion sensor 60 may encompass any structural configuration capable of detecting and measuring blood volume within the target tissue.

During use, the catheter 12 having the first and second optical fibers 56, 58 may be introduced into a selected heart region of a heart chamber through a vein or artery (e.g., the femoral vein or artery) using a suitable percutaneous access technique such that a location suitable for ablation for treatment of the pathology (e.g., ablation therapy) is determined. Although the blood perfusion sensor 60 is shown in the measurement processing system 14, the blood perfusion sensor 60 can also be disposed in any suitable location of the catheter 12, e.g., integrated within or near the electrode tip 16. In another embodiment, the optical fibers 56, 58 are not used if the blood perfusion sensor 60 is directly located at the electrode tip 16.

The measurement processing system 14 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired physiological activity. In some examples, the measurement processing system 14 includes a general purpose microprocessor and/or a specialized microprocessor (e.g., a digital signal processor, or DSP, which may be optimized for processing activation signals) that executes instructions to receive, analyze and display information associated with the received physiological activity. In such examples, the measurement processing system 14 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that measurement processing system 14 can take any suitable form for receiving electrical signals and processing the received electrical signals.

In addition, the measurement processing system 14 may be configured to measure the volume of blood in the myocardial tissue adjacent to the electrode tip 16. For example, the measurement processing system 14 may be configured to detect the blood perfusion associated with the target site of the myocardial tissue. The measurement processing system 14 processes the sensed blood perfusion to generate a display of relevant characteristics. Such processed output may include information relating to blood volume changes, light absorption changes, and the like, in the tissue. The relevant characteristics may assist a user to identify a site suitable for ablation therapy.

The measurement processing system 14 may output data to a suitable device, for example, a display device 62, which may display relevant information for a user. In some examples, the display device 62 is a CRT, LED, or other type of display, or a printer. The device 62 presents the relevant characteristics in a format useful to the user. In some embodiments, the catheter 12 and associated hardware and software (e.g., the measurement processing system 14 and the display 62) can be utilized as a stand-alone measurement system independent of the RF power supply 13 and corresponding hardware and software. In embodiments, the measurement processing system 14 stores, e.g., in memory 64, the relevant information of the blood perfusion, such as the information representing the volume of blood within the target site, for subsequent retrieval by the user.

In embodiments, the memory 64 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like.

In embodiments, the memory 64 stores computer-executable instructions for causing the measurement processing system 14 to implement aspects of embodiments of system components discussed herein and/or to perform aspects of embodiments of methods and procedures discussed herein. The computer-executable instructions may include, for example, computer code, machine-useable instructions, and the like such as, for example, program components capable of being executed by one or more processors associated with the catheter system 10. Program components may be programmed using any number of different programming environments, including various languages, development kits, frameworks, and/or the like. Some or all of the functionality contemplated herein may also, or alternatively, be implemented in hardware and/or firmware.

Figure 2:
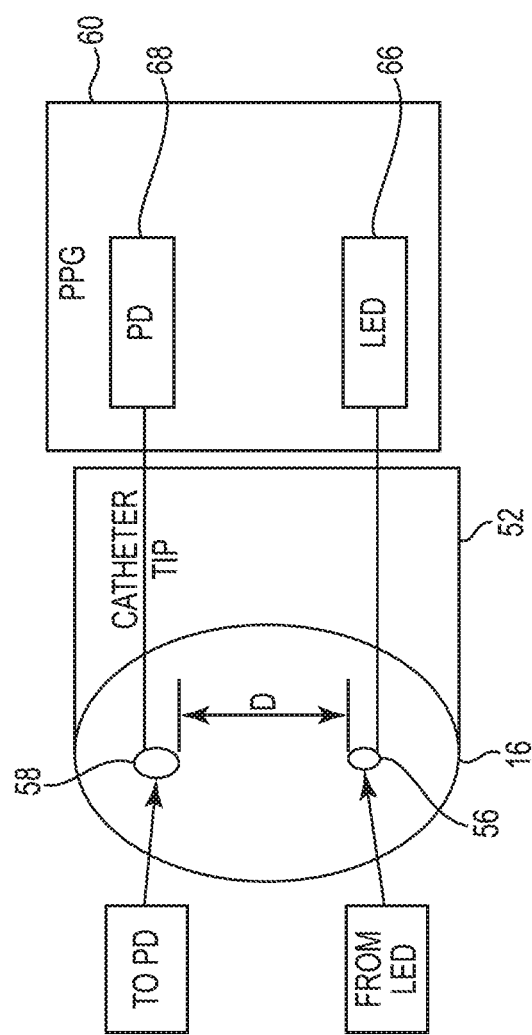
FIG. 2 is a perspective view depicting an exemplary structure of an ablation catheter shown in FIG. 2 in accordance with embodiments of the disclosed subject matter.

FIG. 2 is a simplified schematic showing exemplary structures of the catheter 12 operatively connected to the blood perfusion sensor 60. In one embodiment, the blood perfusion sensor 60 includes a light source 66, such as a light-emitting diode (LED), configured to generate and transmit a first light beam 70, and a light detector 68, such as a photodiode (PD), configured to detect a second light beam 72 that is transmitted or reflected from the target tissue to the PD 68. In the illustrated embodiment, the first optical fiber 56 is configured to transmit the first light beam 70 from the LED 66 into a capillary vessel 74 having one or more hemoglobin cells 76 at the target site of the tissue.

In embodiments, the second light beam 72 is derived from the first light beam 70. For example, when the first light beam 70 is reflected by at least one hemoglobin cell 76, the second light beam 72 is the reflected first light beam 70. The second light beam 72 is then transmitted to the PD 68 via the second optical fiber 58 for further processing. In another example, when the hemoglobin cell 76 is not present at the target site of the tissue, either due to the force applied by the electrode tip 16 or scar tissues adjacent the target site, the second light beam 72 is the first light beam 70 reflected by other portions of the tissue. As such, in some embodiment, the blood perfusion sensor 60 can be used to assess the lesion barriers or formations at one or more target sites in the tissue (e.g., within the heart chambers). In one example, the first light beam 70 reflects differently when the tissue is swollen with an incoming blood flow when the blood perfuses away. At each heartbeat the blood rushes into the tissue swelling it in volume and then relaxes as the blood perfuses away.

In one embodiment, the blood perfusion sensor 60 is configured to compare the first light beam 70 and the second light beam 72 to detect a change in the volume of blood within the target site. In one embodiment, the blood perfusion sensor 60 can compare the first and second light beams 70, 72, e.g. as a ratio. For example, the ratio would act to normalize the output and if measured from a back reflection from the LED 66, a fiber end face would act to eliminate variations due to light loss and/or due to variations in bending of the fiber and LED output variation itself.

The blood perfusion sensor 60 also detects the change in a volume of the tissue at the target site (e.g., blood volume changes) in a microvascular bed of the tissue. In one example, the change in the volume of blood within the target site can be measured based on the change(s) in light absorption detected by the PD 68. An output of the blood perfusion sensor 60, such as an intensity (I) of light relative to time (T), can be displayed on the display device 62 for monitoring purposes. Illustrative graphs representing the intensity (I) and the time (T) are shown in FIGS. 4 and 5. Detailed descriptions of the graphs are provided below in paragraphs relating to FIGS. 4-5.

The degree of blood perfusion in the target tissue derived by the blood perfusion sensor 60 can provide useful information to the clinician during an ablation procedure. For example, FIG. 3 depicts the distortion of the tissue at the target site 80 caused by force or pressure applied to the tissue by the electrode tip 16, thereby compressing the tissue and capillary network within the target site tissue. This force or pressure results in a decrease in blood perfusion in the affected tissue, which can increase the effectiveness of the application of RF ablation energy. In one embodiment, the blood perfusion information can be used as an input to the catheter system 10 to indicate when the RF ablation energy should be applied. In addition, in some embodiment, the blood perfusion sensor 60 can be used to assess the formation of lesions at the target site, as necrosed tissue will exhibit a lower degree of blood perfusion than the adjacent, healthy tissue. the lesion barriers or formations at one or more target sites in the tissue (e.g., within the heart chambers).

In one embodiment, at least one distal end of the corresponding first and second optical fibers 56, 58 can be externally exposed outside of the electrode tip 16. In another example, at least one distal end of the corresponding first and second optical fibers 56, 58 can be internally positioned in the electrode tip 16 (e.g., in the cavity 17). In such a case, a protective window (not shown) configured to transmit the first and second light beams 70, 72 can be mounted at least partially at the electrode tip 16.

In other embodiments (not shown), the LED 66 and the PD 68 can be disposed in the blood perfusion sensor 60. In embodiments, the LED 66 and the PD 68 are proximally and/or selectively positioned from each other within a predetermined distance D (FIG. 3). However, in another embodiment (not shown), the LED 66 and the PD 68 can be disposed in or mounted at a distal end of the catheter 12, e.g., in the electrode tip 16 of the catheter 12. In some embodiments, at least one of the LED 66 and the PD 68 can be disposed in an external portion of the ablation catheter system 10, e.g., in a handle assembly. For example, the LED 66 can be positioned in the cavity 17 but the PD 68 can be positioned in the handle assembly. In another example, both the LED 66 and PD 68 can be inserted in the handle assembly.

FIGS. 4-5 are exemplary graphical representations of changes in light absorption detected by the ablation catheter system 10. In FIG. 4, the blood perfusion sensor 60 measures one or more changes in light absorption at a target site 80 of the tissue based on a pressure generated by the catheter 12. Any changes in the blood perfusion at the target site 80 can be used to determine an extent of the blood perfusion. For example, as shown in FIG. 4, the PD 68 can detect an optical signal 82 representative of the volume of blood within the target site 80 of the tissue. If the second light beam 72 reflected by the hemoglobin cell 76 is transmitted to the PD 68 via the second optical fiber 58, the blood perfusion is not stopped. As shown in FIG. 4, the optical signal 82 includes peaks and valleys representing values of the intensity (I) of the second light beam 72 relative to the time (T), such as a timestamp in real time. In one embodiment, an average value of peaks may represent an overall intensity (I) of the second light beam 72.

However, if the blood perfusion is stopped below the electrode tip 16 at the target site 80 as the pressure is applied by the electrode tip 16 of the catheter 12, the second light beam 72 cannot be transmitted to the PD 68 due to lack of the hemoglobin cells 76 that reflect the first light beam 70. As shown in FIG. 5, the blood perfusion may stop at a predetermined pressure applied by the electrode tip 16, and an optical signal 84 includes a constant value of the intensity (I) of the second light beam 72. When the blood perfusion is stopped, the RF energy applied at the target site 80 becomes more localized, faster, deeper, and more repeatable and/or predictable, thereby enhancing the control of tissue ablation and reducing the overall operation time. Thus, the ablation effectiveness can be monitored by measuring the intensity (I) of the second light beam 72 as the pressure is applied and/or released by the electrode tip 16. In embodiments, the blood perfusion sensor 60 can be used to synchronize ablation pulses so that the heating RF pulse occurs between blood pulses if the pressure is kept low enough to allow blood perfusion. Advantageously, this can be more accurate than using ECG information because of the time lag for blood perfusion.

In some embodiments, a substantial termination of the blood perfusion at the target site 80 may be enough to achieve an effective RF ablation. For example, when the intensity (I) of the second light beam 72 is below (or less than) a predetermined threshold for a predetermined period, the RF energy can be applied at the target site 80. In another embodiment, an estimated oxygen saturation level ($SpO_2$) can also be used with the blood perfusion sensor 60 to indicate the change of the blood flow at the target site 80. For example, when the $SpO_2$ level in the tissue is below a predetermined threshold for a predetermined period, the RF energy can be applied at the target site 80.

Before, during, and after the application of the RF energy, the ablation catheter system 10 can be used to repeatedly remeasure in real time the changes in light absorption at the target site 80. As such, it is easier to control and monitor the tissue ablation and to assess the lesion formation(s) caused by the RF ablation. In various applications, the tissue ablation performed by the ablation catheter system 10 can also be applied in tumor ablation and/or nerve ablation. In the tumor ablation, a blood pulse can be used as a signal that the ablation has been thorough. In the nerve ablation, the tissue ablation can be used in the airways of a patient.

In one embodiment, a slope of the curve shown in FIG. 4 can be used to calculate a rate of blood perfusion within the target tissue. In another example, a blood perfusion rate can be used as an output measurement, e.g., the output is proportional to the blood volume or flow rather than an exact measurement of the volume or flow.

Various wavelengths may be used for the first light beam 70 to suit different applications. A tissue penetration depth is determined based on the respective wavelength of the first light beam 70. For example, the first light beam 70 can be an ultraviolet light with wavelengths ranging from approximately 100 to 380 nanometers (nm), a blue light with wavelengths ranging from approximately 380 to 500 nm, and other visible light rays with wavelengths ranging from approximately 500 to 650 nm, such as a green light, a yellow light, and a red light. In another example, the first light beam 70 can also be a near infrared light with wavelengths ranging from approximately 650 to 750 nm. Other suitable wavelengths above 750 nm are also contemplated to suit the application.

In one embodiment, the blood perfusion sensor 60 includes a single light source, such as the LED 66, configured to generate one or more light beams, each having a different wavelength. Similarly, the blood perfusion sensor 60 includes a single light detector, such as the PD 68, configured to detect one or more light beams, each having the different wavelength. In another embodiment, the blood perfusion sensor 60 includes a plurality of light sources, such as multiple LEDs, configured to generate two or more light beams, each having a different wavelength. Similarly, the blood perfusion sensor 60 includes a plurality of light detectors, such as multiple PDs, configured to detect two or more light beams, each having the different wavelength.

In some embodiments, the blood perfusion sensor 60 can be used or replaced with another suitable type of oxygen saturation sensor. In one example, the oxygen saturation sensor can be a Doppler ultrasound sensor configured to detect the volume of blood within the target site 80, e.g., in the arteries or veins of the tissue. For example, the Doppler ultrasound sensor is configured to measure the blood perfusion at the target site 80 by detecting backscattered light that is Doppler shifted due to a velocity of the moving hemoglobin cells 76 in the tissue. Other suitable non-contact oxygen saturation sensors, such as laser sensors, are also contemplated to suit different applications.

Figure 6:
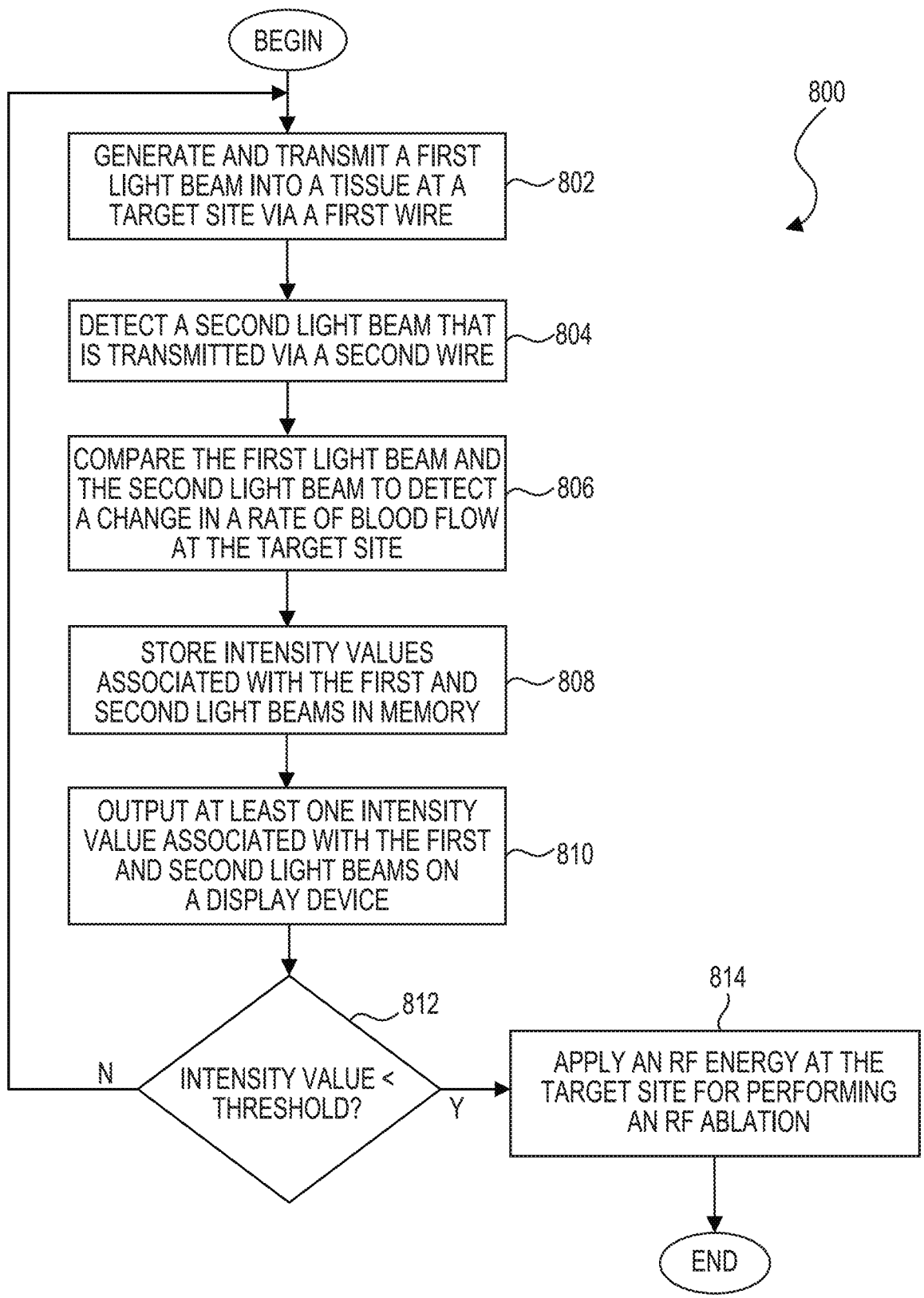
FIG. 6 is a flow diagram depicting an illustrative method of an exemplary process of ablation procedures using the ablation catheter system of FIG. 1 in accordance with embodiments of the disclosed subject matter.

FIG. 6 is a flow diagram showing an exemplary method of blood perfusion measurement and ablation procedures using the ablation catheter system 10. As disclosed herein, the catheter system 10 is not particularly limited and can perform any of the methods described within the scope of this disclosure. In FIG. 6, a method 800 of performing the blood perfusion measurement and ablation procedures is shown using the catheter system 10.

At block 802, the LED 66 of the blood perfusion sensor 60 generates the first light beam 70 and transmits the first light beam 70 into the tissue at the target site 80 via the first optical fiber 56. The first light beam 70 penetrates the tissue at the target site 80 to reach the hemoglobin cell 76 (if there is any) in the tissue.

At block 804, the PD 68 of the blood perfusion sensor 60 detects the second light beam 72 that is transmitted to the PD 68 via the second optical fiber 58. For example, the second light beam 72 may be the first light beam 70 reflected by the hemoglobin cell 76 (if there is any), and the second light beam 72 is carried to the PD 68 using the second optical fiber 58.

At block 806, the blood perfusion sensor 60 compares the first light beam 70 and the second light beam 72 to detect a change in the volume of blood within the target site 80. For example, the blood perfusion sensor 60 detects the change in the volume of blood within the target site tissue based on a change in light absorption detected by the PD 68. In one embodiment, an intensity value of the first light beam 70 and another intensity value of the second light beam 72 are compared to detect the change in the blood perfusion at the target site 80. In another embodiment, the intensity value of the second light beam 72 is compared to a predetermined threshold to detect the change in the blood perfusion at the target site 80.

At block 808, the measurement processing system 14 stores the intensity and time values associated with the first and second light beams 70, 72 in memory 64 for subsequent retrieval. For example, the intensity values correspond to the target site 80 of the tissue, and the intensity values can be recorded in real time for an operational duration of the RF ablation.

At block 810, the measurement processing system 14 outputs at least one of the intensity values associated with the first and second light beams 70, 72 on the display device 62. For example, the intensity value of the second light beam 72 can be displayed on the display device 62 for monitoring purposes during the RF ablation.

At block 812, the measurement processing system 14 determines whether the intensity value of the second light beam 72 is below a predetermined threshold for a predetermined period. When the intensity value of the second light beam 72 is below the predetermined threshold for the predetermined period, control proceeds to block 814. Otherwise, control returns to block 802. For example, at block 802, the LED 66 of the blood perfusion sensor 60 generates the first light beam 70 having a different wavelength than a previous wavelength and retransmits the first light beam 70 into the tissue at the target site 80 via the first optical fiber 56.

At block 814, the ablation catheter system 10 applies the RF energy at the target site 80 for performing the RF ablation. For example, an automatic ablation procedure can be performed by a robotic device, but the user, such as a doctor, can initiate the ablation procedure by operating the ablation catheter system 10. In one embodiment, the user (e.g., a physician) can mark or target one or more ablation regions on the tissue. In another embodiment, identifying and marking the ablation regions can be performed autonomously by the system 10 without manual intervention of the user using the robotic device. Any of blocks 802-814 can be repeated as desired.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A system for performing ablation on a target tissue, the system comprising:
 a catheter including an elongate catheter body having a proximal end and an opposite distal end, and a catheter tip coupled to the distal end of the catheter body and configured to deliver ablative energy to the target tissue;
 a light source configured to generate and transmit a light beam to be directed from the catheter tip toward the target tissue; and
 a blood perfusion sensor operatively coupled to the catheter tip and configured to measure and generate an output representing a degree of blood perfusion within the target tissue when the catheter tip is in contact with the target tissue and to detect a change in the volume of blood within the target tissue resulting from a force applied to the target tissue by the catheter tip, wherein the blood perfusion sensor comprises a light detector configured to detect light reflected from the target tissue during use.

2. The medical system of claim 1, wherein the light source is a light-emitting diode and the light detector is a photodiode.

3. The medical system of claim 1, wherein one or both of the light source and the light detector are disposed within the catheter tip.

4. The medical system of claim 1, wherein the catheter further comprises an optical fiber disposed within the catheter body and the catheter tip and operatively connected to one or both of the light source and the light detector.

5. The medical system of claim 1, wherein the catheter further comprises a first optical fiber disposed within the catheter body and the catheter tip and operatively connected to the light source, and a second optical fiber disposed within the catheter body and the catheter tip and operatively connected to the light detector.

6. The medical system of claim 1, wherein the change in the volume of blood within the target tissue is measured based on a change in light absorption by the target tissue resulting from the force applied to the target tissue by the catheter tip.

7. The medical system of claim 1, further comprising an ablation controller configured to generate and deliver the ablative energy to the catheter tip when the measured degree of blood perfusion is below a pre-determined threshold value.

8. A system for performing ablation on a target tissue, the system comprising:
 a catheter including:
  an elongate catheter body having a proximal end and an opposite distal end;
  a catheter tip coupled to the distal end of the catheter body and configured to deliver ablative energy to the target tissue;
  a first optical fiber disposed within the catheter body and the catheter tip; and
  a second optical fiber disposed within the catheter body and the catheter tip;
 a light source operatively connected to the first optical fiber and configured to generate and transmit a first light beam to be directed from the catheter tip toward the target tissue;
 a light detector operatively connected to the second optical fiber and configured to detect a second light beam that is reflected from the target tissue; and
 a measurement processor operatively connected to the light detector and configured to measure and generate an output representing a degree of blood perfusion within the target tissue when the catheter tip is in contact with the target tissue and to measure a change in blood perfusion within the target tissue based on a change in the volume of blood within the target tissue resulting from a force applied to the target tissue by the catheter tip.

9. The medical system of claim 8, wherein the light source is a light-emitting diode and the light detector is a photodiode.

10. The medical system of claim 8, further comprising an ablation controller configured to generate and deliver the ablative energy to the catheter tip when the measured degree of blood perfusion within in the target tissue is below a pre-determined threshold value.

11. A system for performing ablation on a target tissue, the system comprising:
 a catheter including an elongate catheter body having a proximal end and an opposite distal end, and a catheter tip coupled to the distal end of the catheter body and configured to deliver ablative energy to the target tissue; and
 a blood perfusion sensor operatively coupled to the catheter tip and configured to measure and generate an output representing a degree of blood perfusion within the target tissue when the catheter tip is in contact with the target tissue and to determine whether a blood volume within the target tissue is less than a predetermined threshold for a predetermined period, wherein the blood perfusion sensor comprises a light detector configured to detect light reflected from the target tissue during use.

12. The medical system of claim 11, further comprising a light source configured to generate and transmit a light beam to be directed from the catheter tip toward the target tissue.

13. The medical system of claim 12, wherein the light source is a light-emitting diode and the light detector is a photodiode.

14. The medical system of claim 12, wherein one or both of the light source and the light detector are disposed within the catheter tip.

15. The medical system of claim 12, wherein the catheter further comprises an optical fiber disposed within the catheter body and the catheter tip and operatively connected to one or both of the light source and the light detector.

16. The medical system of claim 12, wherein the catheter further comprises a first optical fiber disposed within the catheter body and the catheter tip and operatively connected to the light source, and a second optical fiber disposed within the catheter body and the catheter tip and operatively connected to the light detector.

17. The medical system of claim 11, wherein the blood perfusion sensor is further configured to detect a change in the blood volume within the target tissue resulting from a force applied to the target tissue by the catheter tip.

18. The medical system of claim 17, wherein the change in the blood volume within the target tissue is measured based on a change in light absorption by the target tissue resulting from the force applied to the target tissue by the catheter tip.

19. The medical system of claim 11, further comprising an ablation controller configured to generate and deliver the ablative energy to the catheter tip when the measured degree of blood perfusion is below a pre-determined threshold value.

\* \* \* \* \*